United States Patent [19]

Bach et al.

[11] Patent Number: 4,722,223

[45] Date of Patent: Feb. 2, 1988

[54] TRANSVERSE VIBRATION APPARATUS FOR GRADING WOOD PANELS

[75] Inventors: Lars Bach, Edmonton; Andrew W. Porter, Richmond, both of Canada

[73] Assignee: Her Majesty the Queen in right of the Province of Alberta as represented by the Minister of Energy & Natural Resources, Edmonton, Canada

[21] Appl. No.: 860,380

[22] Filed: May 6, 1986

[51] Int. Cl.$^4$ .............................................. G01M 7/00
[52] U.S. Cl. ..................................................... 73/579
[58] Field of Search ........................... 73/579, 580, 159

[56] References Cited

U.S. PATENT DOCUMENTS 2,486,984 11/1949 Rowe ..................................... 73/582
3,513,690 5/1970 Pellerin et al. ......................... 73/579

*Primary Examiner*—John Chapman
*Attorney, Agent, or Firm*—Ernest P. Johnson

[57] ABSTRACT

The present invention provides an apparatus and method for establishing a measure of the modulus of elasticity of a wood panel. The apparatus comprises a support frame having a triangular array of panel support points provided thereon. A load cell, in combination with one support point, is interconnected to a frequency counter. This assembly is functional to determine the weight and vibration frequency of a dropped panel. A panel lifting assembly is provided to raise and drop the panel, thereby causing it to vibrate at its natural frequency. In a process aspect, the invention involves supporting the panel at three triangularly arranged support points, raising the panel at the apex end, and dropping the panel to cause it to vibrate at its resonant frequency, and computing a measure of stiffness from the measurements made.

3 Claims, 3 Drawing Figures

TRANSVERSE VIBRATION APPARATUS FOR GRADING WOOD PANELS

FIELD OF THE INVENTION

The invention relates to a method and apparatus for the non-destructive testing of a reconstituted wood panel. More particularly it relates to method and apparatus utilized for measuring the stiffness of the panel.

BACKGROUND OF THE INVENTION

Wood panels, generically termed "reconstituted wood panels", include such fabricated products as plywood, flakeboard, hardboard, particleboard, waferboard, oriented strand board and the like. Such panels are manufactured in the form of large, relatively thin, sheets. Typically, such a panel might be about four feet in width and eight feet in length.

As a consequenc of the process of manufacture, such panels display a greater propensity to warpage and sagging than a natural wood product.

It is desirable, therefore, to be able to establish, relatively quickly and by using a non-destructive testing technique, values for the panel which can be used to calculate a measure of the modulus of elasticity of the panel. It is known that modulus of elasticity (MOE) determined by slow static methods correlates with the modulus of rupture (MOR) of wood based panels.

It is also known, in the prior art, to determine the modulus of elasticity of a thin elongate beam using a transverse vibration technique. This method involves simple support on knife edges across each end of the beam, inducing vibration of the beam and measuring the resonant frequency thereof. The modulus of elasticity is derivable from the equation given herebelow.

$$E_d = \frac{wL^3 f^2}{kbh^3} \quad (1)$$

where
- $E_d$ is the dynamic modulus of elasticity;
- w is the weight of the panel;
- L is the span distance;
- f is the resonant frequency ($H_z$);
- b is the width;
- h is the thickness; and
- k is the constant for mode of vibration and acceleration due to gravity.

However, the acknowledged teaching in the prior art has concluded that the above-cited relationship, whilst applicable to slender beam members is not functional when dealing with enlarged "plate" or panel units. In practical terms, the difficulties of supporting a panel on knife edges across each end, due to the warpage and configuration thereof, and measuring the resonant frequency using prior art techniques, have appeared to prevent vibration being successfully applied to wood panels.

SUMMARY OF THE INVENTION

In accordance with the present invention, transverse vibration of a reconstituted wood panel and measurement of its resonant frequency are utilized to arrive at a measure of the modulus of elasticity of a panel. This measure has been found to correlate well with standard methods employed to determine a measure of the modulus of elasticity. The theoretical relationship between modulus of elasticity and resonant frequency for slender beams would appear to be applicable to large relatively thin panels also.

In the apparatus aspect of the invention, there is provided a support frame having three upstanding point-like members arranged in a triangular pattern. The support points are distanced apart so as to support the underside of the panel adjacent each of two opposed side edges thereof. The apex support point is positioned substantially at the centre line of the panel. The apparatus includes means associated with one of the points for measuring the load of the panel. Preferably such means comprises a load cell. Also, the apparatus includes means for measuring the resonant frequency of the vibrating panel. Preferably, such means comprise a frequency counter or an accelerometer. And finally, the apparatus comprises mechanical means for lifting the panel only at the apex end thereof adjacent its centre line, while said panel remains supported at its opposed end, and dropping the panel, to thereby induce transverse vibration thereof.

In the use of the apparatus, the panel is placed on the points. Its weight is measured. And then the apex end of the panel is lifted and dropped, so as to impact against the apical support point and induce transverse vibration. The frequency of vibration is measured. The obtained data may then be used to compute a measure of the stiffness of the panel.

By using the triangular pattern of support points, the warpage and sagging inherent in the broad thin panel do not prevent the necessary measurements from being made. In addition, it has been found that transverse vibration frequency can be used to yield accurate stiffness values.

DESCRIPTION OF THE PREFERRED EMBODIMENT

Figure 1:
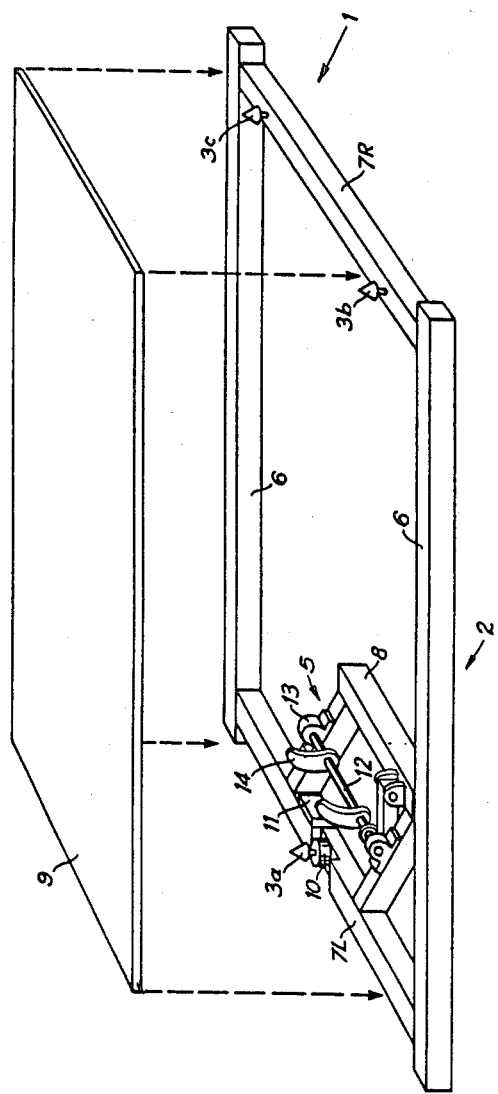
FIG. 1 is a perspective view of an apparatus having a wood panel poised thereabove.
Figure 2:
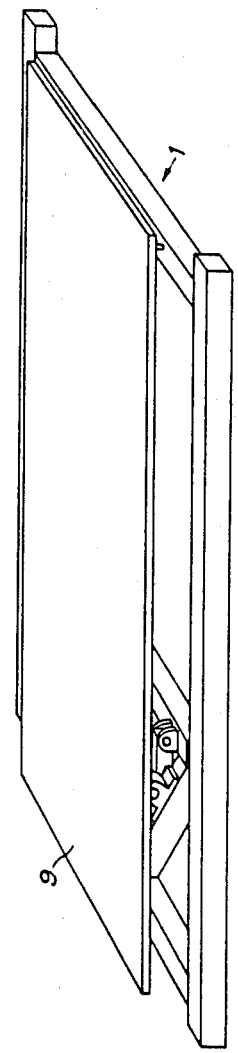
FIG. 2 is a perspective view of the apparatus of FIG. 1 with the panel supported in place.

The transverse vibration apparatus 1 comprises, in general, a frame 2, three support members or points 3a, 3b, 3c, a load-cell/frequency counter assembly 4, and a panel lifting and dropping assembly 5.

The frame 2 is rectangular in form, comprising side beams 6 and transverse end beams 7L, 7R. A downwardly angled, U-shaped subframe 8 is attached to the end beam 7L and extends inwardly therefrom.

The end beams 7L, 7R carry the upwardly projecting points 3a, 3b, 3c. Apical point 3a is positioned at about the middle of frame end beam 7L and base points 3b, 3c are positioned on end beam 7R. As shown, the points are therefore in a triangular pattern. The frame 2 is dimensioned so that the points 3a, 3b, 3c are positioned to support the underside of panel 9 adjacent each of its ends.

The apical support point 3a is the load position of a conventional load cell 10 which is mounted in a recess formed in the end beam 7L. A suitable load cell for this purpose is manufactured by Transducers Inc. of Whither, Calif., under model number C62H-500-10P1.

A frequency counter 11 is operatively connected with the load cell 10, to count the oscillations of the load cell piston. A suitable counter for this purpose is manufactured by Hewlett Packard of Palo Alto, Calif., under model number 5316A.

The combination of the load cell and the frequency counter provides means for determining the weight of the wood panel 9 and its resonant frequency when it is dropped onto the support points 3a, 3b, 3c. It is assumed that the total panel weight is approximately twice that of the load cell weight reading.

An assembly 5 is mounted on the sub-frame 8 for lifting and dropping the panel 9 onto the points 3a, 3b, 3c. The assembly 5 comprises a rotatable shaft 12 journalled in bearings 13 mounted on the sub-frame. The shaft carries a pair of lifting arms 14. Upward rotation of the shaft causes the arms to lift one end of the panel; swift downward rotation of the shaft causes the panel end to drop onto the apical point 3a and to resonate thereon. The shaft 12 can be manually or mechanically actuated in a suitable manner.

Utilizing the formula given herebelow, the measure of stiffness is derivable from the measurements obtained.

$$E_d = \frac{WL^3}{K \cdot B \cdot D^3 \cdot P^2} \quad (2)$$

where
$E_d$ is the modulus of elasticity (in transverse vibration perpendicular to the longitudinal axes and the plane of the panel)
W is the total specimen weight (lbs.)
L is the length of the vibration span (in.)
B is the width of the specimen (in.)
D is the panel thickness (in.)
P is the period of oscillation (1/H$_z$)
K is a constant for the mode of vibration and acceleration due to gravity (g). For simple support as described, g=386 in./sec.$^2$ and first order transverse vibration K equals 79.37.

EXAMPLE

Table 1 given herebelow is included to demonstrate the operability of the above-described apparatus and testing method. The average modulus of elasticity $E_d$ of the two readings A and B obtained by the transverse vibration technique of the present invention are compared to the modulus of elasticity $E_s$ obtained using a standard Post Flexure Machine as described in ASTM D 3043-76 Method C. The two readings A and B are derived from the same panel with different ends being positioned over the load cell.

TABLE 1

| Panel Identification | A × 10$^6$ psi psi | B × 10$^6$ psi psi | AVERAGE × 10$^6$ psi psi | E POST FLEXURE × 10$^6$ psi psi |
|---|---|---|---|---|
| Waferboard ¾" | | | | |
| W1 | 0.72 | 0.74 | 0.73 | 0.70 |
| W2 | 0.74 | 0.72 | 0.73 | 0.76 |
| W3 | 0.73 | 0.72 | 0.73 | 0.77 |
| W4 | 0.69 | 0.71 | 0.70 | 0.71 |
| W5 | 0.71 | 0.72 | 0.72 | 0.78 |
| Average | 0.72 | 0.72 | 0.72 | 0.74 |
| OSB ⅜" | | | | |
| O1 | 1.21 | 1.21 | 1.21 | 1.47 |
| O2 | 1.23 | 1.23 | 1.23 | 1.51 |
| O3 | 1.16 | 1.15 | 1.16 | 1.42 |
| O4 | 1.17 | 1.16 | 1.17 | 1.46 |
| O5 | 1.28 | 1.30 | 1.29 | 1.59 |
| Average | 1.21 | 1.21 | 1.21 | 1.49 |
| Spruce ¾" | | | | |
| S1 | 1.05 | 1.04 | 1.05 | 1.27 |
| S2 | 1.05 | 1.02 | 1.05 | 1.30 |
| S3 | 0.89 | 0.91 | 0.90 | 1.26 |
| S4 | 1.02 | 1.01 | 1.02 | 1.39 |
| S5 | 1.07 | 1.06 | 1.07 | 1.45 |
| Average | 1.02 | 1.01 | 1.02 | 1.33 |
| Fir ⅜" | | | | |
| F1 | 1.46 | 1.38 | 1.42 | 1.83 |
| F2 | 1.12 | 1.13 | 1.13 | 1.41 |
| F3 | 1.09 | 1.09 | 1.09 | 1.43 |
| F4 | 1.22 | 1.22 | 1.22 | 1.39 |
| F5 | 1.20 | 1.20 | 1.20 | 1.60 |
| Average | 1.22 | 1.20 | 1.21 | 1.53 |

The modulus of elasticity values $E_d$ given in Table 1 are derived by substitution of the values set forth in Table 2, given herebelow, in equation 2.

TABLE 2

| Panel Ident. | W$_A$ lbs | W$_B$ lbs | L in | B in | D in | K in/sec | P$_A$ sec | P$_B$ sec |
|---|---|---|---|---|---|---|---|---|
| W1 | 78.68 | 79.42 | 92.0 | 47.50 | 0.730 | 79.37 | .2401 | .2388 |
| W2 | 77.88 | 75.70 | 92.0 | 47.50 | 0.713 | 79.37 | .2456 | .2443 |
| W3 | 78.33 | 76.10 | 92.0 | 47.50 | 0.722 | 79.37 | .2423 | .2415 |
| W4 | 75.16 | 77.79 | 92.0 | 47.50 | 0.723 | 79.37 | .2442 | .2449 |
| W5 | 77.64 | 77.49 | 92.0 | 47.50 | 0.732 | 79.37 | .2391 | .2383 |
| O1 | 67.32 | 67.42 | 92.0 | 47.50 | 0.613 | 79.37 | .2231 | .2232 |
| O2 | 67.62 | 66.98 | 92.0 | 47.50 | 0.608 | 79.37 | .2243 | .2238 |
| O3 | 67.12 | 67.27 | 92.0 | 47.50 | 0.613 | 79.37 | .2282 | .2289 |
| O4 | 67.02 | 66.83 | 92.0 | 47.50 | 0.614 | 79.37 | .2264 | .2263 |
| O5 | 67.92 | 68.76 | 92.0 | 47.50 | 0.602 | 79.37 | .2241 | .2239 |
| S1 | 57.40 | 56.86 | 92.0 | 47.50 | 0.734 | 79.37 | .1689 | .1691 |
| S2 | 49.97 | 49.67 | 92.0 | 47.50 | 0.723 | 79.37 | .1610 | .1629 |
| S3 | 49.27 | 49.72 | 92.0 | 47.50 | 0.726 | 79.37 | .1729 | .1714 |
| S4 | 58.45 | 58.45 | 92.0 | 47.50 | 0.756 | 79.37 | .1653 | .1660 |
| S5 | 59.93 | 59.49 | 92.0 | 47.50 | 0.746 | 79.37 | .1673 | .1673 |
| F1 | 52.69 | 50.51 | 92.0 | 47.93 | 0.583 | 79.37 | .1931 | .1947 |
| F2 | 55.43 | 55.52 | 92.0 | 47.93 | 0.625 | 79.37 | .2016 | .2032 |
| F3 | 51.31 | 51.70 | 92.0 | 47.93 | 0.620 | 79.37 | .2007 | .2018 |
| F4 | 53.24 | 53.04 | 92.0 | 47.93 | 0.621 | 79.37 | .1933 | .1927 |
| F5 | 55.27 | 54.48 | 92.0 | 47.93 | 0.625 | 79.37 | .1964 | .1951 |

Figure 3:
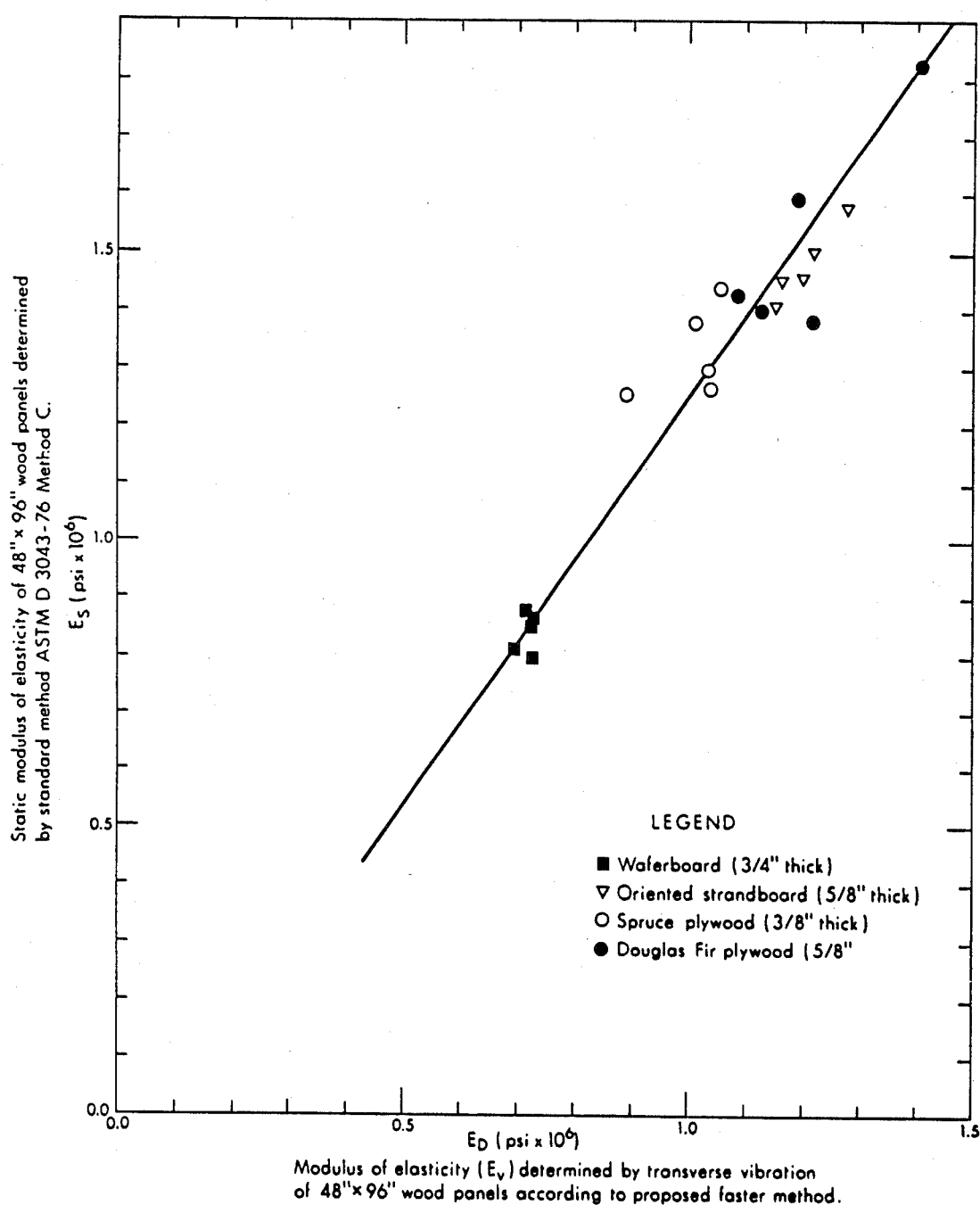
FIG. 3 is a graph depicting a plot of $E_s$ determined by ASTM D 3043-76 method C versus $E_d$ determined by a transverse vibration method.

FIG. 3 illustrates the correlation between the modulus of elasticity as determined by the method described hereabove, versus the static modulus of elasticity determined by the standard ASTM D 3043-76 Method C for panels constructed from various materials.

The embodiments of the invention in which an exclusive property or privilege is claimed are defined as follows:

1. An apparatus for measuring the stiffness of a reconstituted wood panel having first and second opposed ends, comprising:
    a frame;
    first, second, and third panel support points, associated with the frame for bearing upwardly against the underside of the panel, said support points being arranged in a triangular pattern so that the single first support point is positioned at about the center line of the panel adjacent the first end thereof and the pair of second and third support points are positioned close to the panel side edges adjacent the second end of the panel;
    means, associated with one of the support points, for measuring the load of said panel;
    means for measuring the resonant frequency of said panel; and
    mechanical means, associated with the support frame adjacent the first support point, for lifting only at the first end thereof adjacent the panel center line, while it remains still supported at its second end, and dropping the panel onto the first support point to thereby induce transverse vibration thereof, whereby the measurements of weight and vibration frequency may be used to compute a measure of the stiffness of said panel.

2. The apparatus as set forth in claim 1 wherein said load-measuring means comprises a load cell and said means for measuring frequency is a frequency counter.

3. A method for establishing a measure of the stiffness of reconstituted wood panel comprising:
    supporting the underside of a panel, having opposed first and second ends, with a triangular pattern of three support points, so that a single first support point is positioned at about the center line of the panel adjacent the first end thereof and the pair of second and third support points are positioned close to the panel side edges adjacent the second end of the panel;
    lifting only at the first end thereof adjacent the panel center line, while it remains still supported at its second end, and dropping the panel onto the first support point to induce transverse vibration thereof at resonant frequency;
    measuring the resonant frequency of the panel; and
    determining the load of the panel;
    whereby the measurements obtained may be used to compute a measure of the stiffness of the panel.

* * * * *